United States Patent [19]
Jones et al.

[11] Patent Number: 5,324,853
[45] Date of Patent: Jun. 28, 1994

[54] PROCESS FOR THE PRODUCTION OF PLASTICIZER AND POLYOLESTERS

[75] Inventors: Larry O. Jones; Glen W. Davis; John Lyford, IV, all of Baton Rouge, La.; Sun-tsun Fong, Taikoo Shing, Hong Kong; Ramesh R. Hemrajani, Millington, N.J.

[73] Assignee: Exxon Chemical Patents Inc., Linden, N.J.

[21] Appl. No.: 6,228

[22] Filed: Jan. 19, 1993

[51] Int. Cl.$^5$ .............................................. C07C 67/08
[52] U.S. Cl. ........................................ 560/98; 560/99
[58] Field of Search ............................ 560/78, 98, 99

[56] References Cited

U.S. PATENT DOCUMENTS

| | | | |
|---|---|---|---|
| 2,411,136 | 11/1946 | Luce | 260/485 |
| 2,494,133 | 1/1950 | Jefts | 260/475 |
| 2,628,249 | 2/1953 | Bruno, Jr. | 260/475 |
| 3,056,818 | 10/1962 | Werber | 260/410.6 |
| 3,681,434 | 8/1972 | Neely | 260/475 |
| 4,241,216 | 12/1980 | Bergman et al. | 560/99 |
| 4,304,925 | 12/1981 | Watanabe et al. | 560/78 |
| 5,110,508 | 5/1992 | Buettgen et al. | 554/170 |

FOREIGN PATENT DOCUMENTS

| | | | |
|---|---|---|---|
| 0342357 | 4/1989 | European Pat. Off. | C07C 67/69 |
| 1299078 | 12/1972 | United Kingdom | C07C 69/80 |
| 1426057 | 2/1976 | United Kingdom | C07C 69/76 |
| 1565663 | 4/1980 | United Kingdom | C07C 67/08 |

*Primary Examiner*—José G. Dees
*Assistant Examiner*—Samuel Barts
*Attorney, Agent, or Firm*—John J. Mahon

[57] ABSTRACT

A process for the catalytic or non-catalytic esterification of acids or anhydrides with a mono-alcohol or a polyhydroxy compound which comprises the steps of adding the reagents to a reaction vessel to form a reaction mixture, and heating the reaction mixture and maintaining a pressure sufficient to obtain boiling of the reaction mixture thereby causing esterification and removing water as vapor while continuously mixing the reaction mixture in the reactor vessel such that at least about 2.5 to about 20 volumes of reaction mixture are internally recirculated per minute, whereby the rate of conversion is enhanced.

28 Claims, 6 Drawing Sheets

PROCESS FOR THE PRODUCTION OF PLASTICIZER AND POLYOLESTERS

The present invention is directed primarily to a process for preparing plasticizer esters for polyvinylchloride (PVC) such as phthalates, adipates and trimellitates in the presence of a titanium, zirconium or tin-based catalyst or acid catalyst. It is also useful for preparing polyol esters in the presence of excess acid and, optionally, a catalyst. This improved process is capable of producing high quality esters at high rates of conversion.

BACKGROUND OF THE INVENTION

The reaction conditions under which esterification is affected can be varied considerably. The reaction proceeds very slowly at room temperature, but quite rapidly at elevated temperatures. About 99% of the limiting reagent, such as acids, anhydrides or polyols, is converted to an ester within a few hours. Limiting reagents are typically reagents which are not present in stoichiometric excess, e.g., limiting reagents used to make plasticizers include diacids and phthalic anhydride and those used to make polyol esters are polyols.

To facilitate the complete esterification of the reactants, it is desirable that the water which is formed during esterification be removed as rapidly as possible. It is known that water has a detrimental effect upon the rate of conversion. Conventionally, water has been removed by carrying out the reaction in a liquid medium which forms an azeotrope having a boiling point that is lower than that of either component of the reaction. If the resulting ester has a boiling point well above 100° C. at atmospheric pressure, then the reaction temperature can be adjusted such that no liquid medium capable of forming an azeotrope is required.

One conventional process for forming plasticizer esters is disclosed in Great Britain Patent Specification No. 1,426,057 (Imperial Chemical Industries Limited), wherein plasticizer esters are prepared from phthalic anhydride and a $C_4$ to $C_{14}$ alkanol or mixture of such alkanols. For example, a mixture of phthalic anhydride and one or more of these alkanols may be heated gradually up to 180° to 260° C. in the presence of a titanium catalyst (e.g., titanium isopropoxide). When the temperature reaches 180° to 260° C., the esterification is substantially complete although the residual acidity is about 0.3 to 0.05 mg KOH/gram. Aqueous sodium carbonate solution is then slowly added to the ester product to provide 1 to 12 times the stoichiometric amount of alkali. When the temperature has fallen to 150° to 200° C. water or a dilute aqueous alkali solution is admitted and the excess alkanol is removed. By this treatment the titanium catalyst is converted to titanium oxide and precipitated, and thereafter may be filtered off with excess sodium carbonate and the residual acidity is reduced to less than 0.05 mg KOH/gram.

Most esterification processes are capable of converting about 99% of the limiting reagent, such as acids, anhydrides or polyols, to an ester within a few hours; however, after about 90% of the limiting reagent is converted the rate of reaction tends to slow down substantially. It may take half as long again to convert the remaining 4–5% of limiting reagent as it took to convert the initial 95% thereof. Since the chemical industry is continuously seeking to increase the rate of reaction as well as the quality of the resultant esters, it would be quite desirable to develop a process which increases the overall rate of reaction, especially during the esterification of the last 10% of limiting reagent.

In the commercial production of plasticizer esters, e.g., phthalates, adipates, and trimellitates, conversions of greater than 99% and as high as practical are desired. The unreacted portion of the acid or anhydride (i.e., the limiting reagent) will react with base in the final steps of the esterification process and a water soluble salt will be formed that eventually ends up in a waste treatment stream. Thus, an increase from 99.0% to 99.95% conversion reduces waste treatment loads associated with treating unconverted acid or anhydride in plasticizer production by a factor of twenty. In addition, environmental regulations are mandating increases in efficiency of treatment plants. Thus, there is a significant incentive to achieve as high a conversion as possible and reduce the load on existing treatment facilities.

For polyol esters, e.g., esters made from aliphatic acids and trimethyolpropane (i.e., the limiting reagent), the commercially desirable conversions are at greater than 98%. In the case of polyol esters, the excess acid is generally removed by a combination of stripping, neutralization and washing. Thus, the environmental load is determined by the efficiency of stripping prior to neutralization. The conversion level is determined by the product specification for the hydroxyl number, a measure of the number of residual hydroxyl groups in the ester. Typical product applications require conversions of about 98.5% of the original number of hydroxyl groups in the poly alcohol.

It is well known that the amount of water in the esterification reactor at any time is a major factor in determining the overall rate of reaction. The present inventors have developed a novel method by which water in the esterification reactor is removed at a much faster rate than under conventional methods, thereby substantially increasing the overall rate at which the reactants are converted to esters. In general, for a given conversion the lower the water content, the faster the rate of reaction.

The present inventors have modified the conventional esterification process wherein the rate at which water is removed from the reactor is increased to such a degree that the amount of water contained in the reactor after about 90% of the reaction mixture has been converted to an ester is much lower than conventional methods. Modification of other aspects of the process such as neutralization, decolorization or demetalling, water removal, filtration of the ester mixture, steam stripping and filtration of the stripped ester have also been found to enhance the quality of the resultant esters.

The present invention also provides many additional advantages which shall become apparent as described below.

SUMMARY OF THE INVENTION

A process is disclosed for the catalytic or noncatalytic esterification of acids or anhydrides with a mono-alcohol or a polyhydroxy compound which comprises the steps of adding either an acid or anhydride and a mono-alcohol or a polyhydroxy compound to a reaction vessel to form a reaction mixture, and heating the reaction mixture to a temperature in the range between about 150° to 280° C., preferably between about 180° to about 260° C., and maintaining a pressure sufficient to obtain boiling of the reaction mixture thereby causing the esterification and removing water as vapor while continuously mixing the reaction mixture in the reactor vessel such that at least about 2.5 to about 20 volumes of reaction mixture are internally recirculated per minute (defining reactor turnover rate to be the volumes of reaction mixture internally recirculated per minute divided by the reaction mixture volume, continuously mixing the reaction mixture in the reactor vessel to achieve a reactor turnover rate of at least about 2.5 to about 20), whereby the rate of conversion is enhanced and such that for plasticizer esters limiting reagent conversions of greater than 99% are achieved and such that for polyol esters limiting reagent conversions of greater than 98% are achieved. It is still possible to heat the reagents at higher temperatures, such as up to 350° C., so long as the reagents remain stable.

This process may comprise the following additional steps: addition of adsorbents such as alumina, silica gel, activated carbon, clay and/or filter aid to the ester mixture; addition of base to neutralize any residual organic or inorganic acids; filtration of solids from the ester mixture containing the bulk of the excess reagent (i.e., acid or alcohol) used in the esterification process; removal of the excess reagent from the ester mixture by steam stripping under vacuum and recycling of the excess reagent to the reaction vessel; and removing any residual solids from the stripped ester by means of secondary filtration.

In catalytic reactions, the neutralization step may also include the addition of water to hydrolyze the catalyst and, optionally, the addition of activated carbon for color removal. Further, the base may be added as a solution with the water. When hydrolysis occurs the process typically includes the following additional step, i.e., removal of the water used in the hydrolysis step by settling and/or by means of flashing. Optionally, clay or other adsorbent addition may follow water removal.

Optionally, the step of heating the reagents may use a reflux drier or non-reflux drier method for reducing the amount of water refluxed from the vapor taken overhead from the reaction vessel. The reflux drier method includes the additional steps of: passing vapor from the reaction vessel through a packed tower or column such that a portion of excess reagent contained within the vapor is stripped and recycled to the reaction vessel, and wherein the partially stripped vapor is taken overhead; passing the partially stripped vapors through a condenser to an overhead collection drum which allows the excess reagent and the water to separate into two liquid phases; separating the excess reagent from the water; recycling the excess reagent to the packed tower and contacting it with the vapor from the reaction vessel; recycling the water to the hydrolysis step; taking overhead the vapors from the collection drum for condensation of water contained therein; and recycling condensate from the vapors to the hydrolysis step.

The non-reflux drier method includes the following additional steps: passing vapor from the reaction vessel through a condenser and then the condensate is passed to an overhead collection drum which allows the excess reagent and the water to separate into two liquid phases; separating the excess reagent from the water; recycling the excess reagent through a heater and to a flash drum thereby producing a water-rich vapor which is taken out overhead and combined with the vapors from the reaction vessel and an excess reagent-rich liquid which is recycled to the reaction vessel; recycling the water to the hydrolysis step; taking overhead the vapors from the collection drum for condensation of water contained therein; and recycling condensate from the vapors to the hydrolysis step.

Other and further objects, advantages and features of the present invention will be understood by reference to the following specification in conjunction with the annexed drawings, wherein like parts have been given like numbers.

DESCRIPTION OF THE PREFERRED EMBODIMENTS

An esterification process used to make esters such as phthalates, adipates and trimellitates comprises a novel esterification reactor which is capable generating a reactor turnover rate of about 2.5 to about 20, preferably a reactor turnover rate of about 3 to about 20, and most preferably a reactor turnover rate of about 4 to about 20.

This process includes the following steps:

a. esterification of an acid or anhydride with excess alcohols and a titanium, zirconium or tin-based catalyst at a temperature and pressure which permits boiling of the mixture in a reactor having a reactor turnover rate in the range between about 2.5 to about 20;

b. addition of adsorbents such as alumina, silica gel, activated carbon, clay and/or filter aid to the reaction mixture following esterification before further treatment, but in certain cases clay treatment may occur later in the process following either flash drying or steam or nitrogen stripping and in still other cases the clay may be eliminated from the process altogether;

c. addition of water and base to simultaneously neutralize the residual organic acids and hydrolyze the catalyst and, optionally, addition of activated carbon during hydrolysis;

d. removal of the water used in the hydrolysis step by heat and vacuum in a flash step;

e. filtration of solids from the ester mixture containing the bulk of the excess alcohol used in the esterification reaction;

f. removal of excess alcohol by steam stripping or any other distillation method and recycling of the alcohol to the reaction vessel; and g. removing any residual solids from the stripped ester in a final filtration.

This process can also be used to convert polyols and acids to polyol esters. The polyol ester process typically comprises the step of esterification of the starting acid with a polyol and, optionally, a catalyst, in a reactor having a turnover rate in the range between about 2.5 to about 20. It may also include one or more of the following steps: removal of excess acid by nitrogen or steam stripping; addition of adsorbents such as alumina, silica gel, activated carbon, clay and/or filter aid to the reaction mixture following esterification before further treatment, but in certain cases adsorbent treatment may occur later in the process following steam stripping and in still other cases the adsorbent step may be eliminated from the process altogether; addition of water and base to simultaneously neutralize the residual organic acids and hydrolyze the catalyst (if present); filtration of solids from the ester mixture containing the bulk of the excess acid used in the esterification reaction; removal of excess acid by steam or nitrogen stripping under vacuum and recycling of the acid to the reaction vessel; and removing solids from the stripped ester in a final filtration.

This method avoids the need for one or more conventional washing steps to remove excess base, but instead relies on filtration to remove the solids.

The preferred reactants used in these esterification processes are set forth below.

ESTERIFICATION CATALYSTS

Typical esterification catalysts are titanium, zirconium and tin catalysts such as titanium, zirconium and tin alcoholates, carboxylates and chelates. See U.S. Pat. No. 3,056,818 (Werber) which issued on Oct. 2, 1962, and which is incorporated herein by reference.

Typical titanium alcoholates which can be used as catalysts include tetramethyl titanates, tetraethyl titanates, tetrapropyl titanates, tetra-isopropyl titanates, tetrabutyl titanates, tetrapentyl titanates, tetrahexyl titanates, tetra-octyl titanares, tetranonyl titanates, tetradodecyl titanates, tetrahexadecyl titanates, tetraoctadecyl titanares, tetradecyl titanates, tetraheptyl titanates and tetraphenyl titanates. The alkoxy groups on the titanium atom can all be the same or they can be different. The zirconium counterparts of the above alcoholates can be substituted in whole or in part as catalysts.

The titanium carboxylates which serve as esterification catalysts are polymeric materials having at least one acyl group for each titanium atom. Typical titanium acylates which can be employed as catalysts include acylates from 2 to about 18 carbon atoms, such as hydroxy titanium acetate, hydroxy titanium butyrate, hydroxy titanium pentanoate, hydroxy titanium hexanoate, hydroxy titanium octanoate, hydroxy titanium decanoate, hydroxy titanium dodecanoate, hydroxy titanium tetradecanoate, hydroxy titanium hexadecanoate, hydroxy titanium octadecanoate, hydroxy titanium oleate, hydroxy titanium soya acylate, hydroxy titanium linseed acylate, hydroxy titanium castor acylate, hydroxy titanium tall oil acylate, hydroxy titanium cocoanut acylate, methoxy titanium acetate, ethyoxy titanium butyrate, isopropoxy titanium pentanoate, butoxy titanium hexanoate, isopropoxy titanium octanoate, isopropoxy titanium decanoate, isopropoxy titanium dodecanoate, isopropoxy titanium tetradecanoate, isopropoxy hexadecanoate, isopropoxy octadecanoate, isopropoxy titanium oleate, isopropoxy titanium soya acylate, isopropoxy linseed acylate, isopropoxy castor acylate, isopropoxy tall oil acylate, and isopropoxy cocoanut acylate. The alkoxy group of the acylate can vary from 1 to about 20 carbon atoms. The corresponding zirconium carboxylates can be used as catalysts.

Titanium chelates are formed by reacting a titanium compound with a polyfunctional molecule including polyols such as glycols or glycerine and amino alcohols, amino acids, hydroxy acids and polycarboxylic acids. Typical chelated esters which serve as catalysts include tetra-ethylene glycol titanate, tetrapropylene glycol titanate, tetrabutylene glycol titanate, tetra-octylene glycol titanate and tetrapolyethylene glycol titanate, dibutoxy di(ethylene glycol) titanate, di-isopropoxy di-(octylene glycol) titanates, dimethoxy, di-(octylene glycol) titanates, diethyoxy di-(octylene glycol) titanates, tetratriethanol amine titanate, tetratriethanol amine-N-oleate, triethanol amine-N-stearate, triethanol amine-N-linseed acid salt, dibutoxy, dipropoxy, dimethoxy, diethoxy, and other dialkoxy dipropoxy, dimethoxy, diethoxy, and other dialkoxy di-(amino alcohol) titanates. The corresponding zirconium chelates are also useful as catalysts.

Selected acid catalysts may also be used in this esterification process. Some examples of acid catalysts are: sulfuric acid, benzene sulfonic acid, p-toluene sulfonic acid, naphthalene sulfonic acid, aluminum sulfate, aluminum powder, normal decylbenzene sulfonic acid, normal dodecylbenzene sulfonic acid, normal nonylbenzene sulfonic acid, normal octylbenzene sulfonic acid, normal heptylbenzene sulfonic acid, normal hexylbenzene sulfonic acid, normal tridecylbenzene sulfonic acid, normal tetradecylbenzene sulfonic acid, normal dodecane sulfonic acid, normal tridecane sulfonic acid, normal tetradecane sulfonic acid, normal pentadecane sulfonic acid, normal hexadecane sulfonic acid, normal heptadecane sulfonic acid, normal octadecane sulfonic acid, normal nonadecane sulfonic acid, normal eicosane sulfonic acid, 3-methyldodecane sulfonic acid, 3-methyl-5-ethyldecane sulfonic acid, 3-methyldecylbenzene sulfonic acid, 4-ethyloctylbenzene sulfonic acid, phosphoric acid, aromatic phosphonic acids (e.g., organic disulfonic acids, 1,2-ethanedisulfonic acid, 1,3-propanedisulfonic acid, m-benzene disulfonic acid, 2,5-, 2,6-, or 2,7-naphthalene disulfonic acids or mixtures of these isomers, and 3,5-o-xylenedisulfonic acid), acidic formalite resins prepared by reacting an aromatic hydrocarbon, an aidehyde, and sulfuric acid, methane disulfonic acid, methane trisulfonic acid, hydrochloric acid, perfluorinated resin sulfonic acid, acidic ion exchange resins, chlorosulfonic acid, thionyl chloride, boron trifluoride, dihydroxy fluoride, dihydroxy fluoboric acid, and silicon tetrafluoride.

ACIDS

Carboxylic acids which undergo esterification can be aliphatic, cyclo-aliphatic or aromatic, they can be substituted or unsubstituted, saturated or unsaturated, or they can be blends of acids. Representative acids include acetic, hydroxyacetic, chloroacetic, bromoacetic, cyanoacetic, 5-phenylacetic, triphenyl acetic, propionic, halopropionic, lactic, beta-hydroxy propionic, n-butyric, isobutyric, n-valeric, isovaleric, 5-phenyl-n-valeric, n-heptanoic, caproic, pelargonic, caprylic, lauric, palmitic, lignoceric, alpha-hydroxy lignoceric, malonic, succinic, glutaric, adipic, pimelic, azelaic, sebacic, decane-1,10-dicarboxylic, pentadecane-1,15-dicarboxylic, pentacosane-1,25-dicarboxylic, 1,2,3-propane tricarboxylic, citric, acrylic, alpha-chloro acrylic, beta-chloro acrylic, beta-bromo acrylic, beta-phenyl acrylic, methacrylic, vinyl acetic, crotonic, angelic, tiglic, undecylenic, oleic, erucic, linoleic, linolenic, maleic, fumaric, mesaconic, citraconic, itaconic, mucconic, aconitic, myristic, stearic, isostearic, branched $C_5$ and $C_{10}$ (e.g., 3,5,5-trimethylhexanoic) and branched $C_{17}$, $C_{19}$, $C_{21}$, etc., acids.

Among the alicyclic acids are cyclopropane carboxylic, cyclobutane carboxylic, cyclopentane carboxylic, cycloheptane carboxylic, cyclohexane carboxylic, 2-hydroxy cyclohexane carboxylic, 1,1-cyclopropane dicarboxylic, 1,2-cyclobutane dicarboxylic, 1,3-cyclobutane dicarboxylic, 1,4-cyclohexane dicarboxylic, cyclohexane-1,2,3,4,5,6-hexacarboxylic, cyclopentene-2-carboxylic, 1-cyclohexene-1-carboxylic, hydrocapric, cyclohexadiene-1,2-dicarboxylic, and 1,3-cyclohexadiene-1,4-dicarboxylic.

The aromatic acids include benzoic, o-, m- and p-chloro and bromo benzoic, o-, m- and p-hydroxy benzoic, o-, m- and p-nitrobenzoic, o-, m- and p-methoxy benzoic, alpha-napthoic, beta-naphthoic, o-, m- and p-methyl benzoic, o-, m- and p-ethyl benzoic, p-phenyl benzoic, phthalic, isophthalic, terephthalic, hydroxy phthalic, 2,3-dimethyl benzoic, benzene-1,2,4-tricarboxylic, benzene-1,3,5-tricarboxylic, benzene-1,2,4,5-tetracarboxylic, diacids of naphthalenes and trimellitic.

When polyols are used to form an ester the following acids are preferred: neopentanoic acid, neoheptanoic, neo-octanoic acid, neononanoic acid, neodecanoic acid, 2-ethyl hexanoic acid, oxo-heptanoic acid (i.e., a mix of isomers derived from oxonation/oxidation of hexenes), oxo-decanoic acid (i.e., a mix of isomers derived from oxonation/oxidation of mixed nonenes), oxo-octanoic acid (i.e., a mix of isomers derived from oxonation/oxidation of mixed heptenes), 3,5,5-trimethylhexanoic acid, linear $C_5$-$C_{18}$ alkanoic acids, and blends thereof.

ANHYDRIDES

Anhydrides of mono and dibasic acids can be used in place of the acids, especially when plasticizer esters are being formed. These include acetic anhydride, propionic anhydride, n-butyric anhydride, succinic anhydride, glutaric anhydride, adipic anhydride, pimellic anhydride, maleic anhydride, mesaconic anhydride, citraconic anhydride, glutaconic anhydride, itaconic anhydride, phthalic anhydride, benzoic anhydride, nadic anhydride, methyl nadic anhydride, hexahydrophthalic anhydride, trimellitic anhydride and mixed anhydrides of monobasic acids. Another anhydride is pyromellitic dianhydride.

ALCOHOLS

Among the alcohols which can be reacted with acids and anhydrides are, by way of example, most primary and secondary C1-C30 monohydric, substituted or unsubstituted alkanols and alkenols, such as, methanol, ethanol, chloroethanol, cyanoethanol, ethoxy-ethanol, phenylethanol, n-propanol, 2-chloropropanol-1, 3-bromopropanol-1, 2,2-dichloropropanol-1, isopropanol, propanol-2, 2-nitrobutanol-1, 2-nitrobutanol-1, 2-methylpentanol-1, 2-methyl pentanol-3, the primary and secondary octanols, n-dodecanol, 6-dodecanol, lauryl, myristyl, stearyl, 2-propenol-1, 2-butenol-1, 3-pentenol-1, ethylene glycol, trimethylene glycol, tetramethylene glycol, pentamethylene glycol, glycerol, 1,4-butanediol, mono and technical grade (i.e., 88% mono, 10% di and 1-2% tri) pentaerythritol, decane-1,10-diol, pentadecane-1,15-diol, pentacosane-1,25-diol, 2,4-hexadiene-1,6-diol, 2,4-octadiene-1,8-diol, and aromatic alcohols such as benzyl alcohol, o-, m- and p-methoxy alcohol, o-, m- and p-nitrobenzyl alcohol, o-, m- and p-methyl benzyl alcohol, phenyl ethyl alcohol, triphenyl ethyl alcohol, o-, m- and p-benzyl benzyl alcohol, alpha-naphthyl-ethyl alcohol, beta-naphthyl ethyl alcohol, naphthylene-1,2-diethyl alcohol, phenylene-1,3,5-triethyl alcohol, and phenylene-1,4-dioctyl alcohols. This includes higher Guerbet alcohols which are beta carbon branched dimer alcohols having ten to twenty-six carbon atoms.

Polyols (i.e., polyhydroxy compounds) are represented by the general formula:

$R(OH)_n$ wherein R is an alkyl, alkenyl or aralkyl hydrocarbyl group and n is at least 2, and can be used in place of the mono alcohols when polyol esters are desired. The hydrocarbyl group may contain from about 2 to about 20 or more carbon atoms, and the hydrocarbyl group may also contain substituents such as chlorine, nitrogen and/or oxygen atoms. The polyhydroxy compounds generally will contain from about 2 to about 10 hydroxy groups and more preferably from about 2 to about 6 hydroxy groups. The polyhydroxy compound may contain one or more oxyalkylene groups and, thus, the polyhydroxy compounds include compounds such as polyetherpolyols. The number of carbon atoms and number of hydroxy groups contained in the polyhydroxy compound used to form the carboxylic esters may vary over a wide range.

The following alcohols are particularly useful as polyols: neopentyl glycol, 2,2-dimethylol butane, trimethylol ethane, trimethylol propane, trimethylol butane, mono pentaerythritol, technical grade pentaerythritol, dipentaerythritol, ethylene glycol, propylene glycol and polyalkylene glycols (e.g., polyethylene glycols, polypropylene glycols, polybutylene glycols, etc., and blends thereof such as a polymerized mixture of ethylene glycol and propylene glycol).

The method according to the present invention is capable of forming plasticizer esters, such as, phthalates, adipates and trimellitates, from $C_4$-$C_{15}$ alcohols, preferably $C_6$-$C_{13}$ oxo-alcohols. Because of the increase in the rate of reaction, in accordance with this invention, the process is particularly useful in esterifications catalyzed by titanium, zirconium, or tin containing catalysts.

This method, with or without the above mentioned titanium, zirconium, or tin based catalysts, is also useful in forming polyol esters, such as, neopolyol esters, from polyols and excess fatty acids. The polyol or polyol mixture is preferably technical grade pentaerythritol (PE), trimethyolpropane (TMP), and neopentylglycol each which can be admixed with monopentaerythritol and/or trimethylol propane or other neopolyols. The preferred acid component is typically a mixture of straight chain acids having five to ten carbon atoms, or a branched chain acid having from five to eighteen carbon atoms, preferably five to nine carbon atoms, namely 2-methylhexanoic, 2-ethylpentanoic, 3,5,5-trimethylhexanoic acids or mixtures thereof. Generally, the acids are monocarboxylic acids. Suitable straight chain acids include, but are not limited to, valeric acid ($C_5$), oenanthic acid ($C_7$), caprylic acid ($C_8$), pelargonic acid ($C_9$), and capric acid ($C_{10}$).

The branched chain acid may be iso-$C_5$, iso-$C_7$, iso-$C_8$ or iso-$C_9$. Preferably, the branched chain acid used is the iso-$C_7$ acid. Another preferred branched acid is 3,5,5-trimethylhexanoic acid derived from the oxonation/oxidation of di-isobutylene. Still another preferred branched acid is oxo-octanoic acid derived from the oxonation/oxidation of mixed heptenes.

In the reaction used to form esters, the acid mixture is present in an excess of about 10 to 50 mole percent or more for the amount of polyol used. The excess acid is used to force the reaction to completion. The composition of the feed acid is adjusted so as to provide the desired composition of product ester. After the reaction is complete, the excess acid is removed by stripping and additional finishing.

The present inventors have developed a novel method capable of minimizing the water level in the reaction vessel, i.e., by controlled mixing in the reaction vessel having particular internal design parameters. Conventional reactors boil (i.e., form vapors) only in the first few inches of liquid depth because the pressure seen by the lower liquid depths quickly exceeds the total vapor pressure of the liquid. In esterifications, water removal is by vaporization together with the excess reagent from the upper boiling region. The present inventors have discovered that in order to remove water most efficiently it must be transported to the upper boiling region by forced convection using a reactor impeller. They have also discovered that an impeller with a large pumping capacity is required in order to minimize concentrations of water (and thereby to increase reaction rates) in the bottom non-boiling regions of the reaction vessel.

In addition, the mixing equipment (i.e., impellets and baffles) must be designed to minimize, as much as possible, the internal recirculation to the impeller. This means that the liquid from the bottom of the reactor must be brought near the surface before returning or recirculating to the impeller blades which are disposed within the lower non-boiling regions.

In order to increase the rate of water removal and thereby reduce the amount of water in the reaction mixture liquid phase at any one time, it is preferable to have a reactor turnover rate of at least about 2.5 (i.e., 2.5 volumes of reactor liquid pumped per minute) and a maximum reactor turnover rate of about 20, above which micro-homogeneity is achieved.

The following text including mathematical models, examples and discussions defines and illustrates the effect of mixing, and hence the relative water concentration and consequent rate of reaction between boiling and non-boiling liquid regions in the reaction vessel, on the time to reach a specific conversion. As such, it can be shown that the present invention reduces batch time to reach the desired conversion and thereby increases reactor productivity.

The below mathematical mixing model was created by the present inventors to assist in determining the reactor turnover rate which would result in reduced water content and thus produce high quality esters at high rates of reaction at conversion above 90%.

Figure 1:
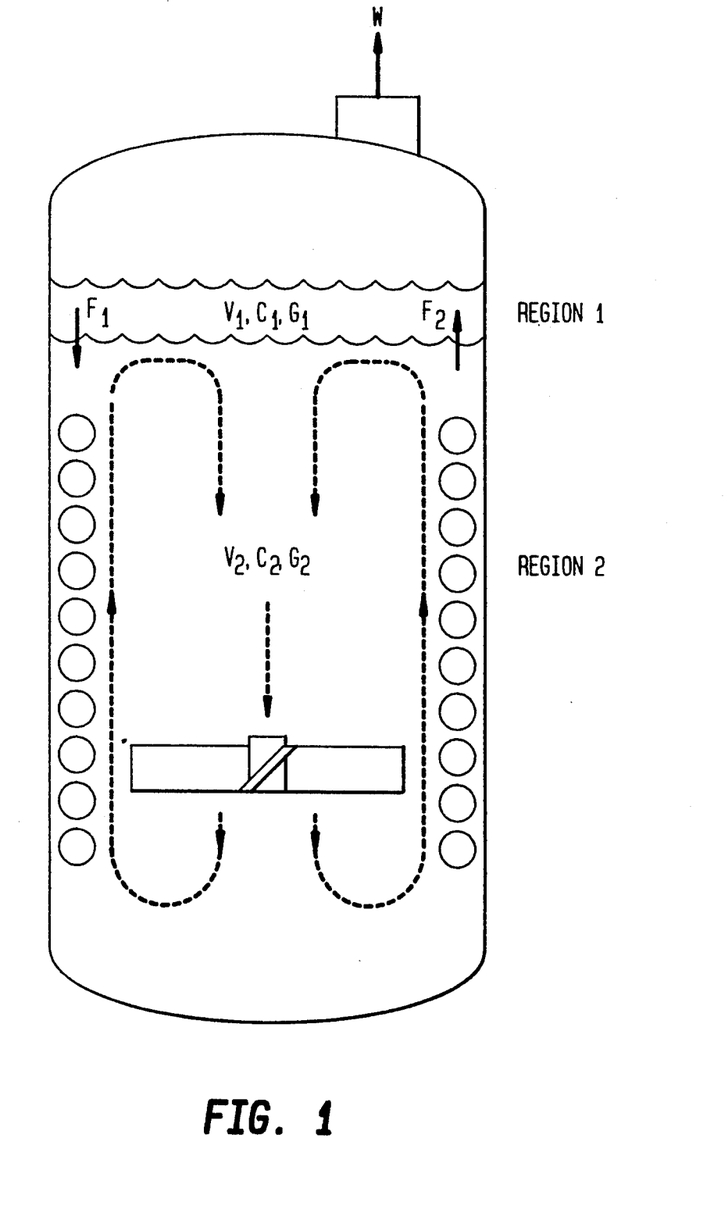
FIG. 1 illustrates a model for internal mixing within a reactor and for removal of water formed during esterification.

An esterification reaction vessel such as that shown in FIG. 1 can be characterized as having at least two well mixed regions, i.e., a well mixed upper boiling region at the surface (Region 1) and a well mixed lower non-boiling region at the bottom (Region 2). A calculation using ideal VLE (i.e., vapor/liquid equilibrium) data shows that boiling can occur in the bulk liquid only near the surface in the first few inches of depth under typical plasticizer reaction conditions. Assume that the pumping action of the impeller displaces liquid from one region to another. The variables are defined as follows:

| | | |
|---|---|---|
| V1 | $m^3$ | Volume of liquid in boiling Region 1 |
| V2 | $m^3$ | Volume of liquid in non-boiling Region 2 |
| C1 | kg $H_2O/m^3$ | Concentration of water in Region 1 |
| C2 | kg $H_2O/m^3$ | Concentration of Water in Region 2 |
| G1 | kg $H_2O$/min./$m^3$ | Generation rate of water in Region 1 |
| G2 | kg $H_2O$/min./$m^3$ | Generation rate of water in Region 2 |
| F1 | $m^3$/min. | Flow rate of solution from Region 1 into Region 2 |
| F2 | $m^3$/min. | Flow rate of solution from Region 2 into Region 1 |
| W | kg $H_2O$/min. | Evaporation rate of water from Region 1 |
| V | $m^3$ soln. | Volume of liquid in vessel: V1 + V2 |
| F/V | 1/min. | Reactor Turnover Rate |

For simplicity, assume that $G1=G2=G$ and that $F1=F2=F$. The rate of water generation can be determined from the esterification kinetics, since one mole of water is made for each mole of phthalic anhydride converted to diester.

For writing the mass balances, assume steady state, i.e., no significant concentration changes in Regions 1 or 2.

A water balance on Regions 1 and 2 gives:

$$F(C2-C1)+G1.V1-W=0$$

$$-F(C2-C1)+G2.V2=0$$

By adding these two equations, we see that the removal of water (W) is equal to the generation of water in Regions 1 and 2.

The difference in water concentration between Regions 1 and 2 can be simply expressed as:

$$C2-C1=G2.V2/F=(W-G1.V1)/F$$

Or, the concentration difference depends on the ratio of the water generation rate in Region 2 times the volume in Region 2 divided by the flow rate between regions. Since V2 is very large compared to V1 and hence V2 is nearly V, the concentration difference is (G)(V)/F or the water generation rate (G) divided by the reactor turnover rate (F/V).

Multiple mixing regions are created in the reactor by using either a single straight blade turbine or multiple pitched or straight blade turbines. The above analysis can easily be extended to multiple regions. When this is done, the water concentration difference for three regions (i.e., a boiling region, and two well mixed non-boiling regions of equal volume created by locating a straight blade turbine in the center of the reactor) is as follows:

$$C3 - C1 = (1 + \tfrac{1}{2})G \cdot V/F$$

Or, for the three region case, the predicted difference between the top and bottom region is 1.5 times greater than the prediction for the two region case.

The general case for N regions (i.e., one boiling region and N-1 well mixed non-boiling regions of equal volume created by using multiple impellers in the reactor) is:

$$CN - C1 = [(1 + 2 + \ldots + (N-1))/(N-1)] \cdot G \cdot V/F$$

Thus, the mathematical mixing model shows that in order to minimize the water concentration in the reactor, the number of well mixed zones in the reactor should be a minimum, or equal to two, as per the above mixing model definitions.

Figure 2:
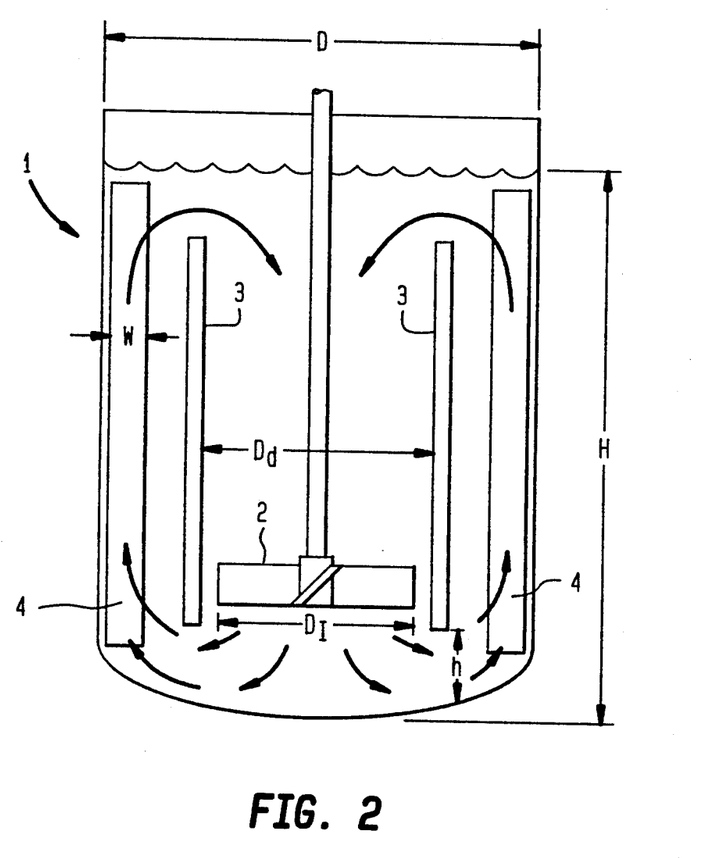
FIG. 2 is the reaction vessel according to the present invention which improves water removal capability during esterification.

The preferred reactor mixing scheme is to have a reaction vessel 1 as shown in FIG. 2, attached hereto, with a height (H) to diameter (D) ratio of less than 1.4 and equipped with a single axial flow impeller 2 pumping downwards. Reaction vessel 1 preferably has a capacity of greater than 7,600 liters (i.e., 2,000 gallons) and a height (H) of at least 1.5 meters (i.e., 5 feet). The direction of the liquid flow is indicated by the arrows disposed within reaction vessel 1. Impeller 2 can be either a pitched blade turbine or, for more streamlined flow, a hydrofoil type turbine. Optionally, a draft tube 3 having a diameter ($D_d$) is centered in the reaction vessel such that the bottom of draft tube 3 extends below impeller 2. A heating coil, not shown, which is normally affixed near the side wall of reaction vessel 1 could, optionally, be disposed around impeller 2 in place of draft tube 3. Impeller 2 is located $\frac{1}{4}$ to $\frac{1}{3}$ of the vessel diameter (D) from the bottom of the dished head. Thus, diameter ($D_d$) is greater than diameter ($D_I$) of impeller 2 and about equal to 0.7 times the diameter (D) of reaction vessel 1. Further, diameter ($D_d$) is such that the cross-sectional area of draft tube 3 and the annular region between draft tube 3 and wall of reaction vessel 1 are equal. The distance (h) from the bottom of draft tube 3 to the bottom of reaction vessel 1 is such that the surface area of a cylinder of height (h) and diameter ($D_d$) is greater than or equal to the cross-sectional area of draft tube 3. The important design concern is to eliminate flow restrictions to prevent eddies. Four wall baffles 4 are spaced equi-distant around reaction vessel 1 and typically have a width (W) 1/10th to 1/12th of the diameter (D) of reaction vessel 1. Wall baffles 4 are used to minimize surface turbulence and vortex formation. Low surface turbulence is desired to promote disengagement of vapor bubbles from the bulk liquid.

Example 1 below demonstrates the effect of mixing on water concentration in reactor top and bottom regions.

EXAMPLE 1

Phthalic anhydride and 20% molar excess of isodecyl alcohol were reacted together in a standard esterification apparatus equipped with a sample tube to make di-isodecyl phthalate. Tetra-isopropyl titanate (TITP) was added at 0.135% by weight on phthalic anhydride at a run time of 95 minutes. The batch was heated to 220° C. while continuously removing the water of reaction and gradually lowering the pressure to maintain the desired temperature. Samples were then removed periodically to measure conversion and water concentration. The data for this example are set forth below in Table 1.

TABLE 1

| MIXING MODEL DEMONSTRATION | | |
|---|---|---|
| Run Time (min) | Percent Conversion | Water (ppm) |
| 0 | 11.4 | 458 |
| 20 | 37.5 | 596 |
| 35 | 51.7 | 460 |
| 50 | 64.9 | 151 |
| 65 | 71.2 | 77 |
| 80 | 76.5 | 62 |
| 95 | 79.2 | 63 |
| 105 | 87.2 | 87 |
| 120 | 95.94 | |
| 140 | 99.63 | 44 |
| 170 | 99.91 | |

Figure 3:
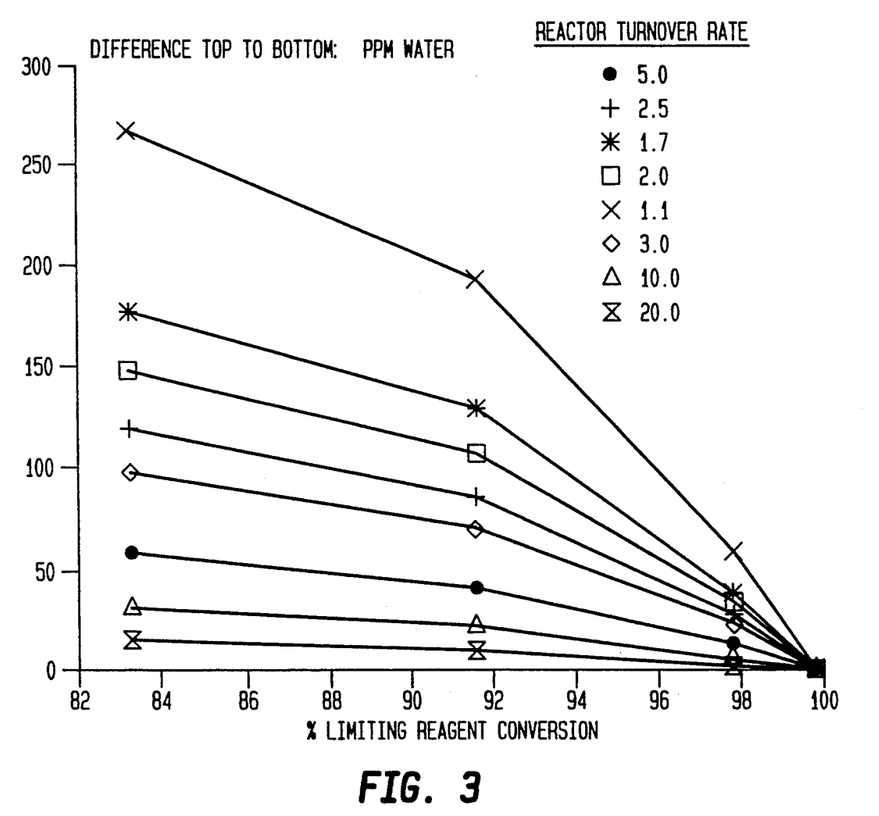
FIG. 3 is a graph plotting the difference in water concentration between the top and bottom regions of the reactor and illustrates the effect of reactor turnover rate on this difference. The ordinate scale from 0–300 is the water concentration in the bottom region minus the water concentration in the top region in parts per million (ppm). The abscissa scale from 82 to 100 is the conversion of the limiting reagent. The parameter for the various curves is reactor turnover rate and it ranges from 1.1 for the top curve to 20 for the bottom curve.

The conversion to phthalate diester and water concentration data in Table 1 above were averaged over each sample period to obtain average rate of reaction data. From this averaged data, the average moles of water formed per minute were calculated and used in the mathematical mixing model to calculate the difference in water concentration between the upper boiling region and the lower non-boiling region in the reactor for different liquid turnover rates as per the mixing model described above. The results of this calculation are illustrated in FIG. 3, attached hereto and tabulated below in Table 2.

In Table 2, the water concentration difference (Region 2 — Region 1) is tabulated as a function of reactor turnover rate and at two levels of conversion of phthalic anhydride (the limiting reagent in this case) to diester. FIG. 3 shows that at 83% conversion of the limiting reagent the water concentration difference increases from about 15 to about 265 as the reactor turnover rate decreases from 20 to 1.1. FIG. 3 also shows that the difference in water concentration between Regions 1 and 2 is high at low conversion (i.e., high water generation rate) and goes to zero as the reaction nears 100% conversion. However, in nearly all of the conversion range of interest, i.e., conversions greater than 90%, the water concentration differences are significant. For example, from the data in Table 2; at 91.5% conversion the difference in water concentration between Region 1 and 2 ranges from 11 ppm at a turnover rate of 20 to 193 ppm at a turnover rate of 1.1. Similarly, at 97.8% conversion, the water concentration difference between Region 1 and Region 2 increases from 3.3 ppm at a turnover rate of 20 to 13 ppm at a turnover rate of 5 to 60 ppm at a turnover rate of 1.1.

TABLE 2

| Reactor Turnover Rate (1/minute) | Concentration Difference (ppm) [Region 2-Region 1] | |
|---|---|---|
| | 91.5% Conv | 97.8% Conv |
| 1.1 | 193 | 60 |
| 1.7 | 128 | 40 |
| 2.0 | 107 | 33 |
| 2.5 | 86 | 27 |
| 3.0 | 71 | 22 |
| 5.0 | 43 | 13 |
| 10.0 | 21 | 6.7 |
| 20.0 | 11 | 3.3 |

Conventional esterification reactors are designed to have a turnover rate of less than 2. Thus, for the reaction rates in this example and at 91.5% conversion of the limiting reagent, conventional reactors would have at least 107 ppm more water in the non-boiling lower region than at the boiling upper region. At reactor turnover rates of 2.5 and 3.0, the difference is reduced substantially to 86 and 71 ppm, respectively. This is a reduction of 21 and 36 ppm, respectively, compared to the conventional reactor having a turnover rate of less than 2.

Achievement of micro-homogeneity sets the upper turnover rate limit for mixing- Micro-homogeneity is nearly achieved at a turnover rate of 20 for typical plasticizer viscosities, i.e., less than 50 centipoise, at typical reaction conditions.

Example 2 below demonstrates the effect of water concentration on the rate of reaction.

EXAMPLE 2

Phthalic anhydride and an isodecyl alcohol were added together in a standard esterification apparatus equipped with a sample tube. A titanium tetra-isopropyl titanate catalyst was added when the batch reached 160° C. The batch was heated to 200° C. while continuously removing the water of reaction and gradually lowering the pressure to maintain the desired temperature. Samples were removed periodically to measure conversion and water concentration. The data presented in Table 3 below is the simple average between the two nearest data points. Reaction condition, i.e., the temperature, pressure, and the amount of feed and catalyst charged were the same for Runs 1 and 2.

TABLE 3
(RATE DATA VS. WATER CONCENTRATION AND % CONVERSION)

| Run No. | Temperature | Conversion | Rate | Water |
|---|---|---|---|---|
| 1 | 200° C. | 99.5 | 0.05 | 20 |
| 1 | 200° C. | 99.0 | 0.1 | 20 |
| 1 | 200° C. | 95.0 | 0.5 | 50 |
| 1 | 200° C. | 90.0 | 0.7 | 75 |
| 2 | 200° C. | 99.5 | 0.02 | 80 |
| 2 | 200° C. | 99.0 | 0.04 | 85 |
| 2 | 200° C. | 95.0 | 0.1 | 130 |
| 2 | 200° C. | 90.0 | 0.2 | 200 |

Notes:
(1) Conversion as mole percent of phthalic anhydride converted to a diester.
(2) Rate of Reaction as percent conversion per minute.
(3) Water Concentration in ppm.

Based upon the above data, the water level in the reaction vessel should be maintained as low as possible, i.e., preferably less than 100 ppm, towards the end of the esterification conversion step, i.e., after about 90% of the ester has formed. As demonstrated in Table 3 above, when the water concentration in the reaction vessel is reduced as in Run No. 1 the rate of reaction is substantially increased. Compare Run No. 1 at 95.0% conversion which has approximately 50 ppm of water and exhibits a rate of reaction of 0.5% per minute with Run No. 2 at 95.0% conversion which has approximately 130 ppm of water and exhibits a much slower rate of reaction, i.e., 0.1% per minute. At 95% conversion, Run No. 1 exhibited a rate of reaction five times as fast as Run No. 2. At 99.0% conversion Run No. 1 had 20 ppm of water and a rate of reaction of 0.1% per minute versus Run No. 2 which had 85 ppm and a rate of reaction of 0.04% per minute. Thus, at 99.0% conversion Run No. 1 exhibited a rate of reaction two and a half times as fast as Run No. 2. Clearly, the run which included the lower water concentrations exhibited substantially higher rates of reaction.

EXAMPLE 3

Phthalic anhydride and a 20% molar excess of isodecyl alcohol were reacted together to make di-isodecyl phthalate in a standard esterification apparatus equipped with a sample tube. Tetra-isopropyl titanate at 0.25 weight percent on phthalic anhydride was added when the batch reached 160° C. Water of reaction was removed continuously and the pressure was adjusted to maintain the desired temperature of 220° C. Samples were removed periodically to measure both water concentration and conversion of the limiting reagent (i.e., phthalic anhydride). The data for this example, as presented in Table 4 below, start at an elapsed time of 70 minutes when a constant temperature of 220° C. was achieved. The final water concentration achieved is 40 ppm.

TABLE 4
(CONVERSION AND WATER CONCENTRATION)

| Tie (min.) | Percent Conversion | Water (ppm) |
|---|---|---|
| 70 | 74.40 | 349 |
| 80 | 86.60 | 174 |
| 85 | 93.80 | 125 |
| 95 | 99.08 | 51 |
| 115 | 99.93 | 40 |
| 145 | 99.95 | 40 |

Figure 4:
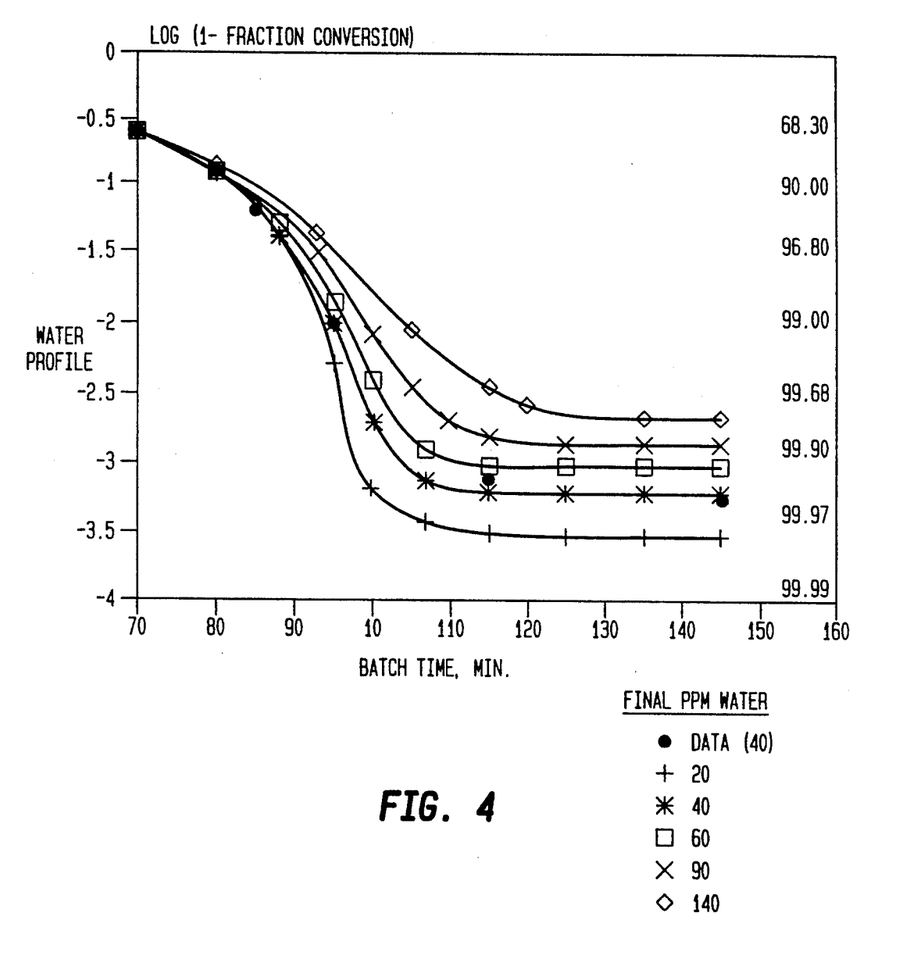
FIG. 4 is a plot showing the effect of water concentration in the reaction mixture on the batch time to needed to reach a particular conversion. The abscissa is the batch reaction time in minutes. The left ordinate scale from minus four (−4) to zero (0) is the common log (base ten) of one minus the fraction conversion. The right ordinate scale marking is percent conversion. For comparison, the ordinate value of minus two (−2) corresponds to a conversion of 99%. The five curves illustrate the effect of five different water concentration profiles on conversion with batch time. The legend indicates the final water concentration for each curve.

A model for esterification kinetics that includes the effects of alcohol concentration, catalyst concentration, and water concentration was developed and the data from Example 3 was used to determine the kinetic constants in the model. Then, the kinetic model was integrated over time to determine the conversion of phthalic anhydride, the limiting reagent, as a function of batch time for different water concentration profiles. FIG. 4 illustrates the fit of the model to the experimental data from Table 4. The experimental data in Table 4 is represented by the filled circles in FIG. 4. The corresponding model calculation is the curve designated as having 40 ppm final water concentration. Additionally, the curves in FIG. 4 illustrate the results from the kinetic model calculations for the effect of the water concentration on batch time to reach a particular conversion. The water profiles, used in the kinetic model calculation, and the corresponding reaction conversions are tabulated below in Table 5 as a function of batch reaction time. Each curve in FIG. 4 has a constant difference in water concentration from any other. For example, the bottom curve (20 ppm final water) has a constant difference of 20 ppm water less than the next curve above (40 ppm final water) for any particular batch reaction time. Batch times for the tabulated data in Table 5 are selected to correspond to the batch time for the data in Example 3 above as tabulated in Table 4 above.

TABLE 5

(CONVERSION AND WATER CONCENTRATION)

| Time (min.) | 20 ppm | | 40 ppm | | 60 ppm | | 90 ppm | | 140 ppm | |
|---|---|---|---|---|---|---|---|---|---|---|
| | % Conv. | Water (ppm) | % Conv. | Water (ppm) | % Conv. | Water (ppm) | % Conv. | Water (ppm) | % Conv. | Water (ppm) |
| 70 | 74.24 | 329 | 74.06 | 349 | 74.12 | 369 | 73.58 | 399 | 73.15 | 449 |
| 80 | 88.33 | 154 | 87.89 | 174 | 87.89 | 194 | 80.99 | 224 | 80.32 | 274 |
| 85 | 93.47 | 105 | 92.92 | 125 | 92.69 | 145 | 91.70 | 175 | 90.65 | 225 |
| 95 | 99.47 | 31 | 99.01 | 51 | 98.60 | 71 | 97.81 | 101 | 96.70 | 151 |
| 115 | 99.97 | 20 | 99.94 | 40 | 99.91 | 60 | 99.5 | 90 | 99.67 | 140 |
| 145 | 99.97 | 20 | 99.94 | 40 | 99.91 | 60 | 99.87 | 90 | 99.79 | 140 |

EXAMPLE 4

Phthalic anhydride (PAN) and isodecyl alcohol (IDA) in the molar ratio of 1:2.5 were reacted together at 220° C. without removal of water until equilibrium was established. The final measured composition was 0.0 moles of phthalic anhydride, 0.2 moles of monoester (ME) (i.e., the reaction product of one phthalic anhydride and one alcohol), 0.8 moles of diester (DE) (i.e., isodecyl phthalate), 0.7 moles of isodecyl alcohol, and 0.875 moles of water. The reaction sequence can be represented as: one mole of phthalic anhydride and one mole of isodecyl alcohol react to form one mole of monoester; and one mole of monoester and one mole of isodecyl alcohol react to form one mole of isodecyl phthalate and one mole of water ($H_2O$). Since no phthalic anhydride is found at the end of the reaction, the first reaction goes to essentially 100% completion. However, for the second reaction in the sequence an equilibrium between reactants and products exists that can be represented by an equilibrium constant defined as $K_{eq}$=[DE].[H2O]/[ME].[IDA] where the brackets, [ ], denote "concentration of". For example, [DE] is equal to 0.8, the concentration of DE at the end of the experiment. The value for $K_{eq}$ for this experiment is 5.0.

Using the value of Keq determined in Example 4, the equilibrium conversions corresponding to Example 3 can be calculated and are compared in Table 6.

TABLE 6

| Water Conc. (ppm) | Equilibrium Frac. Conv. from Ex. 4 | Frac. Conv. at 145 min. from Ex. 3 |
|---|---|---|
| 20 | 0.9997 | 0.9997 |
| 40 | 0.9994 | 0.9994 |
| 140 | 0.9980 | 0.9979 |

Thus, we have demonstrated that the kinetic reaction model used in this Example correctly predicts the effect of water on conversion and that equilibrium was achieved between 115 and 145 minutes for all the cases tested.

A comparison of the experimental data in Table 4 with the model calculations in Table 5, for the same water concentration profile, demonstrate that the model has a good fit with the experimental data. The data in Example 4 demonstrates that the model is an accurate predictor of the effect of water concentration on conversion. Thus, the model can be used, as in this example, to demonstrate the effects on the batch reaction time of changing the water concentration profile.

FIG. 4 demonstrates that the time to achieve a specific conversion of the limiting reagent increases as the water concentration increases. The flatness of the conversion curve at batch times greater than 130 minutes shows that the reaction mixture is very near chemical equilibrium. Thus, the final conversion achievable at chemical equilibrium decreases as the water concentration increases. It shows that the effect of water concentration differences on the time to reach a specific conversion can be detected at conversions greater than 90%. It also demonstrates that water concentration differences of as low as 10–20 ppm water cause significant differences in the batch reaction time to reach commercially desirable conversion, i.e., conversions greater than 99% and more preferably conversions greater than 99.9% and most preferably conversions greater than 99.95%. Specifically, for the given conditions of Example 3, to reach 99.84% conversion (i.e., log(1−conv.)=−2.8) requires 98 minutes for 20 ppm final water, 101.3 minutes for 40 ppm final water, 106 minutes for 60 ppm final water, and 125 minutes for 90 ppm final water. For a water concentration of 140 ppm at the end of the reaction, the equilibrium conversion is 99.78% conversion (i.e., log(1−conv.)=−2.66). The 99.84% conversion level cannot be achieved for 140 ppm final water concentration for the given concentration of catalyst and alcohol in the present example. Again, for the given conditions of Example 3, to reach 99.94% conversion (i.e., log(1−conv.)=−3.2) requires 101 minutes for 20 ppm final water and 113 minutes for 40 ppm final water. For the reaction conditions of Example 3 and for 20, 40, 60, 90, and 1240 ppm final water concentration, the equilibrium conversions based on the esterification kinetics model are respectively 99.97, 99.94, 99.91, 99.87, and 99.79 percent.

In summary, the above models, examples and calculations demonstrate the following: (a) increasing the reactor turnover rate over the standard value of 2 for a typical commercial esterification reactor significantly reduces the water concentration in the bottom well mixed non-boiling zone or zones of the reactor compared to the top zone where boiling occurs (i.e., in Example 1 at 91.5% conversion the concentration difference is reduced from 107 ppm at a reactor turnover rate of 2 to 71 ppm at a turnover rate of 3 to 43 ppm at a turnover rate of 5); (b) multiple well mixed zones in the non-boiling region of the reactor, created by using a straight blade turbine or multiple straight or pitched blade turbines, will increase this difference for a given reactor turnover rate by a minimum factor of 1.5; (c) a particular reactor configuration minimizes both the formation of multiple well mixed, non-boiling zones in the reactor and the internal recirculation to the impeller (FIG. 2); (d) increases in water concentration were found to significantly decrease the reaction rate above 90% conversion (i.e., by a factor of 2.5 for an increase of 60–65 ppm at 99.0 to 99.5% conversion (see Example 2, Table 3); and (e) the percent of time to change the conversion from 75 to 99.84% in Example 3, increases by 11, 29, and 96% for increases in the water concentration profile by 20, 40, and 70 ppm, respectively (see FIG. 4).

In order to demonstrate the invention, the above examples establish the effect of water on batch reaction time by comparing constant differences in water concentration with batch reaction time. In contrast, the mixing model shows that as the conversion nears 100%, the water concentration difference between top and bottom regions decreases because the reaction rate and hence rate of water formation slows. However, significant batch reaction time reduction does occur from the invention, because increasing the reactor turnover rate to between 2.5 and 20 (compared to the typical value of less than 2) significantly reduces the water concentration in the lower non-boiling region during most of the conversion range where water concentration affects the rate, i.e., when the conversion is between 90% (the conversion for which the water concentration begins to affect the rate of reaction as per FIG. 4) and at least 99%. The shortest possible batch reaction time is achieved by minimizing the accumulated time average difference in water concentration between the upper boiling region and the lower non-boiling region.

The above examples, mathematical models, calculations, and discussions demonstrate the invention and illustrate the importance of (1) maximizing the pumping capacity of the impeller (i.e., high reactor turnover rate), (2) minimizing the number of mixing regions and (3) minimizing the short circuiting to the impeller of the liquid flow in the reactor. These considerations are reflected in the recommended design and capability of the mixing system, i.e., a single pitched blade or hydrofoil type turbine delivering a reactor turnover rate of at least about 2.5 to about 20, more preferable 3 to 20, and most preferable 4 to 20, and, optionally, a draft tube to minimize the short circuiting of liquid flow to the impeller.

The batch time may also be reduced by increasing the amount of the excess reagent, increasing the amount of catalyst, or increasing the temperature. However, each of these techniques have limits induced by practicality. Excess reagent must be removed and recycled. Also, increasing excess reagent reduces reactor capacity. Catalysts are costly and must also be removed and safely disposed. Temperature is limited by the available heat source and/or the stability of the product under reaction conditions.

However, the effect of reducing the difference in water concentration between the top and bottom regions of the reactor by maintaining the reactor turnover rate in accordance with this invention can be enhanced by using such other means to increase the rate of the reaction because both the rate of water generation and the difference in water concentration between the top and bottom regions of the reactor is proportional to the rate of reaction.

Production of phthalate esters, as in the above examples, sets the basis for the above discussion. However, in general, all esterification reactions conform to the same effects of water (i.e., water is a reaction product and can take part in the reverse hydrolysis reaction of the ester to acid and alcohol). Thus, the same relative effects of mixing on the rate of reaction and the subsequent reduction in batch time will be true for all esterification reactions and in particular for the types of esters discussed previously above, i.e., adipates, trimellitates, and various types of polyol esters.

Thus, in general, the reduction of water in the bottom region of the reactor relative to the top region by increasing the reactor turnover rate will be observed even with changes in other factors that can change the rate of reaction such as temperature, excess reagent concentration, and catalyst concentration. In addition, the mixing effect holds for all esterification reactions where water is released as a by-product.

Further, this mixing concept holds for any chemical reaction that proceeds with the production of a by-product where the by-product can participate either in a reverse reaction to form the initial reaction products or in other reactions to form unwanted reaction products and where the by-product is removed by distillation.

EXAMPLE 5

Phthalic anhydride and isodecyl alcohol were added together with tetra-isopropyl titanate catalyst in a standard esterification process to form di-isodecyl phthalate.

Water and base were added to the ester to simultaneously neutralize the residual organic acids (resulting from incomplete conversion) and hydrolyze the catalyst. The water and base can optionally be added sequentially.

However, the preferred method is to add the base as a dilute solution in a required amount of water. The preferred base is sodium carbonate. In this instance, a dilute solution of soda ash is used which contains only enough soda ash to equal 1.5 to 2 times the acid value of the residual monoester. The amount of water is from 1.5 to 6 percent of the crude ester weight. The acceptable temperature range is from 90° to 140° C. and above. However, the preferred temperature is 120° C. in order to limit containment pressure. The pressure requirement is determined by the vapor pressure of free water and is about 155 cm Hg (i.e., 5 psia) for 120° C.

It has been discovered that the direct addition of dilute solutions of soda ash is preferred and has particular advantages over caustic or additions of solid soda ash of equal weight. For example, the filtration time for soda ash neutralized esterification was less than for those neutralized with caustic. In fact, the treatment temperature of 120° C. was far above that achievable with caustic. In addition, it is clearly evident from Table 7 below that caustic at low temperatures leads to higher filtration resistance.

TABLE 7

| RUN | BASE | TIME TO REACH FILTERED VOLUME | | | |
| --- | --- | --- | --- | --- | --- |
| | | 500 ml | 1000 ml | 1500 ml | 2000 ml |
| 1 | NaOH | 4 min | 15 min | | |
| 2 | NaOH | 4 min | 15 min | | |
| 3 | Na$_2$CO$_3$ | 2 min | 6 min | 11 min | 17 min |
| 4 | Na$_2$CO$_3$ | 2 min | 6 min | 13 min | 21 min |

As shown in Table 8 below, this process is able to neutralize with soda ash using only 1.5 to 2 times the stoichiometry of the organic acid (i.e., one mole of acid per mole of soda ash) and from 1.5 to 6% water (based on the unstripped reaction mixture). It has also been discovered that carbon can be added before the start of hydrolysis. Thus, decoloring can occur at the same time as the neutralization and hydrolysis.

TABLE 8
EFFECT OF NEUTRALIZATION CONDITIONS ON COLOR, ACIDITY AND FILTRATION RESISTANCE

| Run No. | Temp. (°C.) | Excess Soda Ash[1] | Water % On Batch Weight | Neutralization Results (Acidity as Percent of Filtr. Phthalic Acid) | | | Color Before Neut. | After Neut. |
|---|---|---|---|---|---|---|---|---|
| | | | | Initial | Final[3] | Res.[2] | | |
| 5 | 70 | 1.7 | 1 | 0.0199 | 0.0046 | 265 | NA | NA |
| 6 | 90 | 2 | 2 | 0.0076 | 0.0017 | 46 | 20 | 15 |
| 7 | 120 | 2.3 | 2 | 0.0093 | 0.0027 | 18 | 20 | 15 |
| 8 | 140 | 2 | 2 | 0.0200 | 0.0023 | 18 | NA | NA |
| 9 | 120 | 4 | 2 | 0.007 | 0.0027 | NA | 30 | 20 |
| 10 | 120 | 8 | 2 | 0.0053 | 0.001 | 19 | 25 | 20 |
| 11 | 120 | 2 | 1.5 | 0.0058 | 0.0026 | NA | 30 | 20 |
| 12 | 120 | 2 | 6 | 0.006 | 0.002 | NA | NA | NA |
| 13 | 120 | 2 | 2 | 0.0156 | 0.0033 | 23 | 40 | 15 |
| 14 | 120 | 1.2 | 2 | 0.0526 | 0.0027 | NA | 80 | 20 |

Notes:
(1) The excess soda ash is depicted as the number of stoichiometric equivalents of $Na_2CO_3$.
(2) Relative values for filtration resistance are based on particular measurement units.
(3) Final acidity after neutralization and before stripping excess alcohol.
(4) Color change (Pt/Co ASTM D1209) during neutralization and flash removal of water, but before removal of excess alcohol. Treatment is 0.1% carbon on batch weight.

A color reduction of 20 to 30 units was typical for carbon added at 0.1% based on batch weight. In addition, the titanium levels are reduced to typically less than 1 ppm by the hydrolysis treatment. Titanium is precipitated in an insoluble form and is removed from the system during the filtration step. However, there is usually some residual sodium remaining after the neutralization, flash, and filtration steps. The successful simultaneous neutralization, decoloring and catalyst hydrolysis is achieved by the particular combination of temperature, base choice, and water/base concentrations and residence time. The particular advantages for this operation would not be achieved without the particular combination of factors that we have found. These advantages are low residence time, complete catalyst removal, low acidity, and eliminating a separate decoloring step.

The water is removed before filtration by flashing as rapidly as possible. In the continuous esterification process the flash occurs across a valve. In a batch esterification process the flash is accomplished by dropping the pressure as rapidly as possible. In order to have a low filtration resistance, the water concentration must be below 1000 ppm and preferably below 500 ppm. In addition, if the water is removed in stages, then the filter cake resistance is increased to unacceptable levels. This flash drying is accomplished in the presence of carbon, titanium solids from the hydrolysis, solid soda ash precipitated from the aqueous phase during the flash and any filter aid or clay that was added.

EXAMPLE 6

Di-isodecyl phthalate was prepared in a pilot plant using 20–30 mole percent excess isodecyl alcohol with tetra-isopropyl titanate catalyst. The data set forth in Table 9 below demonstrates the advantages of removing the water prior to filtration as rapidly as possible and to as low a level as possible, whereby low filtration resistance occurs. In all of the runs, water and excess soda ash were added to the reactor at 120° C. and 258.55 cm Hg (i.e., 50 psig) pressure. The batch was stirred until neutralization was complete. After neutralization, for Runs 1 and 2, vacuum was applied. Samples were taken after water had stopped coming off and the temperature reached 120° C. In Runs 3 and 4, the pressure was reduced in stages to achieve intermediate levels of water for the filtration tests.

TABLE 9

| RUN NO. | TEMP. °C. | EXCESS SODA ASH | WATER (%) | IMPELLER RPM | RXN CONV. (%) | FINAL WATER (PPM) | TOTAL TIME (MIN) | FILTRATION[1] RESISTANCE (× .001) |
|---|---|---|---|---|---|---|---|---|
| 1 | 120 | 2 | 2 | 120 | 99.8 | 531 | 40 | 23 |
| 2 | 120 | 2 | 2 | 120 | 99.8 | 143 | 40 | 15 |
| 3 | 120 | 1.62 | 2 | 165 | 99.92 | 1950 | 15 | 226 |
| | | | | | | 1500 | 23 | 220 |
| | | | | | | 760 | 30 | 109 |
| | | | | | | 280 | 40 | 109 |
| 4 | 120 | 1.67 | 2 | 90 | 99.93 | 2086 | 15 | 239 |
| | | | | | | 1014 | 30 | 359 |
| | | | | | | 605 | 37 | 178 |
| | | | | | | 532 | 45 | 175 |
| | | | | | | 409[2] | 90 | 106 |
| | | | | | | 353[3] | 122 | 76 |

Notes:
(1) Relative values based on particular measurement units.
(2) 0.2% clay added to the batch before filtration.
(3) 0.06 filter aid added to the batch before filtration.

We found that the most effective way to produce an easily filterable cake was to reduce the water as rapidly as possible in one step. In run nos. 3 and 4 in Table 9 above where the water was reduced sequentially to 2000, 1500, 700 and 500 ppm, the filter cake resistance was increased to unacceptable levels. Thus, to achieve an acceptable filtration resistance, the water should be removed to below 1000 ppm, preferably below 500 ppm and most preferably in one flash step.

It was discovered that steam sparged into the filtered crude from the flash step would remove metals. A precipitate was formed during the stripping and the filtered plasticizer was free of metals within the accuracy of the analytical method. Nitrogen is a preferable stripping gas. After complete alcohol removal, some residual sodium remains. However, all the sodium is removed from solution when steam is used.

Figure 5:
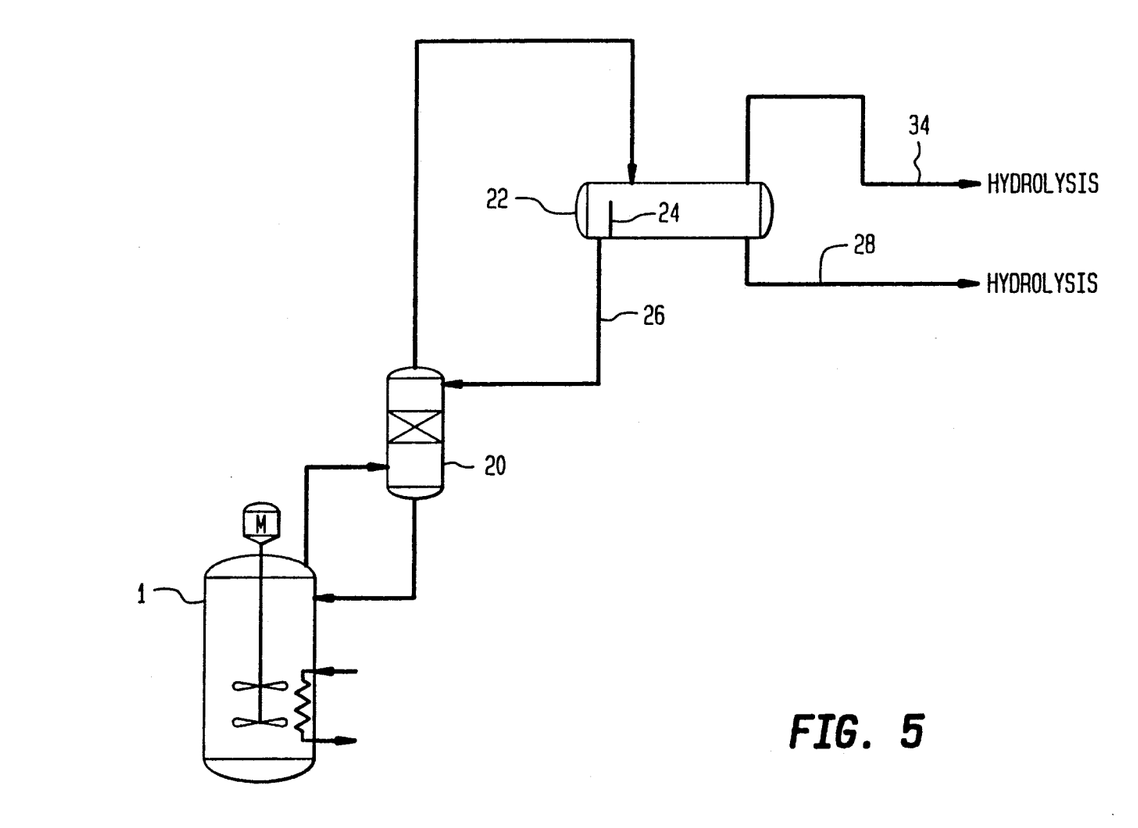
FIG. 5 is a schematic representation of the modified excess reagent recycle portion of the esterification process with a reflux drier.
Figure 6:
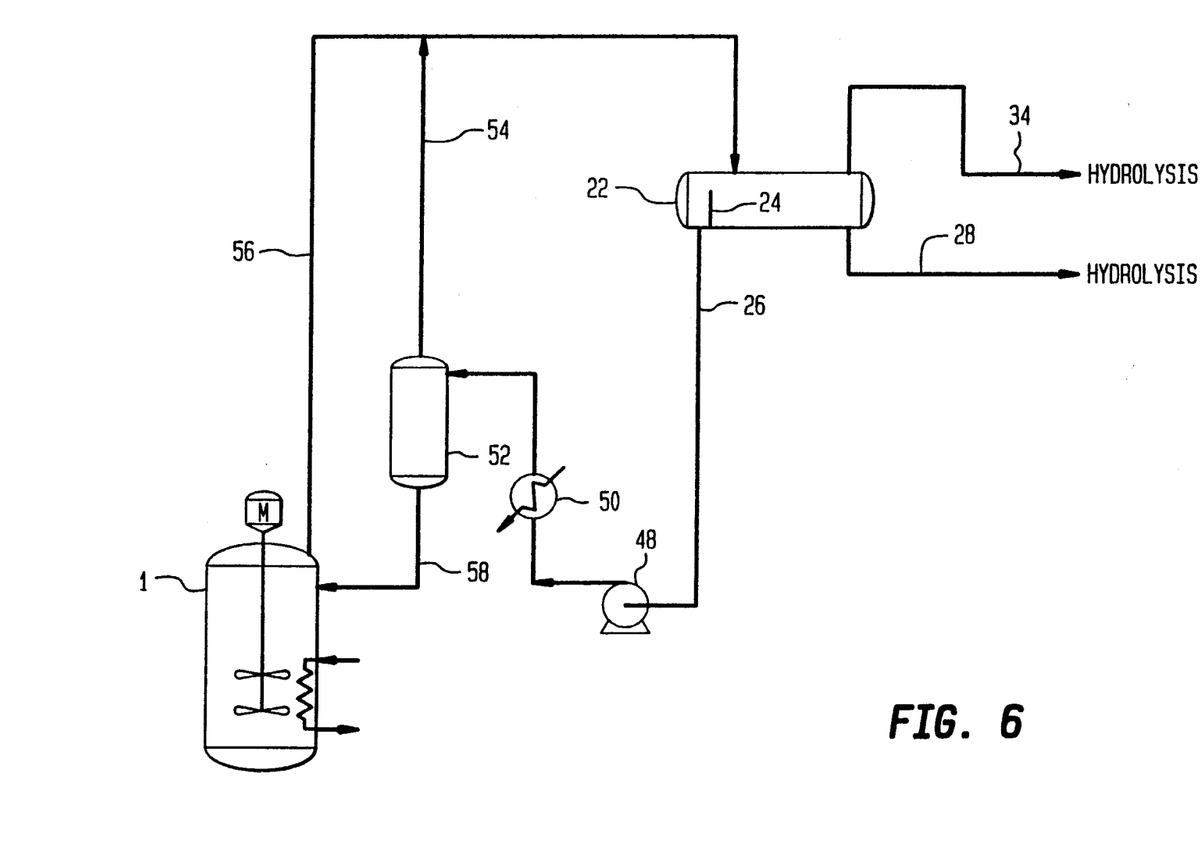
FIG. 6 is a schematic representation of the modified excess reagent recycle portion of the esterification process with a flash drum in place of the reflux drier.

Another unique aspect of the process for esterification developed by the present inventors is the heating step which has been modified such that excess alcohol is refluxed back to the reaction vessel in either of two ways as demonstrated in FIGS. 5 and 6, attached hereto. Both alternative designs reduce the water level in the alcohol which is refluxed back to the reaction vessel and therefore reduce the cycle time in the reaction vessel.

The first alternative design for alcohol recovery is depicted in FIG. 5 which includes a packed tower or column 20 disposed above reaction vessel 1. Packed tower 20 preferably includes one or two theoretical stages with low pressure drop stainless steel packing. The vapors from reaction vessel 1 pass up tower 20 and contact with alcohol from the overhead collection drum 22. Collection drum 22 is a three phase horizontal settling drum which allows the alcohol and water to separate into two liquid phases. Drum 22 operates on phase level control. That is, the alcohol phase overflows weir 24 and is either recycled to reaction vessel 1 or sent to tankage via conduit 26. The water phase is drawn off the bottom through conduit 28 and recycled to the hydrolysis step. Vapor is dragon overhead via conduit 34, condensed and recycled to the hydrolysis step.

FIG. 6 depicts another design which heats the recycle alcohol being returned to reaction vessel 1 without the need for a reflux drier. This design takes into consideration the large variation in vapor rates. In this design the alcohol is pumped via pump 48 from overhead collection drum 22 through conduit 26 and heated in heat exchanger 50. The alcohol is then flashed in alcohol flash drum 52 to remove water. Flash drum 52 pre-heats the alcohol to flash temperature. This temperature will be set by either desired water level or maximum temperature attainable by medium pressure steam. Alcohol flash drum 52 flashes the alcohol to reactor pressure and removes water-rich alcohol overhead. The water-rich vapor is taken overhead from drum 52 via conduit 54 and combined with the overhead discharged from reaction vessel 1 via conduit 56. The alcohol-rich liquid is returned to reaction vessel 1 via conduit 58.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A process for the esterification of acids or anhydrides with a mono-alcohol or a polyhydroxy compound which comprises the following steps:
   a. adding either an acid or anhydride and a mono-alcohol or a polyhydroxy compound to a reaction vessel to form a reaction mixture; and
   b. heating said reaction mixture and maintaining a pressure sufficient to obtain boiling of said reaction mixture thereby converting said acid or anhydride to an ester and removing water as vapor while continuously mixing said reaction mixture in said reactor vessel such that at least about 2.5 volumes of reaction mixture are internally recirculated per minute, whereby the rate of conversion is enhanced.

2. The process according to claim 1 further comprising the addition of a catalyst to said reaction vessel such that said acid or anhydride is catalytically converted to said ester.

3. The process according to claim 2 wherein said catalyst is selected from the group consisting of titanium, zirconium and tin-based catalysts.

4. The process according to claim 2 wherein said catalyst is an acid catalyst.

5. The process according to claim 2 wherein after 95% of said acid or anhydride is converted to said ester the water level in said reaction vessel is maintained below about 100 ppm.

6. The process according to claim 2 further comprising adding water subsequent to heating step (b) so as to hydrolyze said catalyst.

7. The process according to claim 1 wherein said polyhydroxy compound is an aliphatic polyhydric alcohol comprising about 2 to about 10 primary hydroxyl groups.

8. The process according to claim 7 wherein said polyhydroxy compound is selected from the group consisting of neopentyl glycol, 2,2-dimethylol butane, trimethylol ethane, trimethylol propane, trimethylol butane, mono pentaerythritol, technical grade pentaerythritol, dipentaerythritol, ethylene glycol, propylene glycol, and polyalkylene glycols.

9. The process according to claim 1 wherein said reaction vessel includes one boiling upper region and at least one non-boiling lower region, wherein water removal is by vaporization from said upper region.

10. The process according to claim 9 wherein said reaction vessel includes a mixing means which is capable of internally recirculating at least 2.5 volumes of reactor liquid per minute, said mixing means comprising a reactor impeller and at least one baffle disposed about the side wall of said reaction vessel.

11. The process according to claim 10 wherein said mixing means further comprises a draft tube disposed about said impeller.

12. The process according to claim 11 wherein said draft tube is formed from either a flat sheet or heat coils.

13. The process according to claim 10 wherein water is transported from said at least one non-boiling lower region to said upper boiling region by means of forced convection using said reactor impeller.

14. The process according to claim 10 wherein said reactor impeller is capable of minimizing the internal recirculation of said reaction mixture such that said reaction mixture from said lower region of said reaction vessel is recirculated to said upper region before it returns to said reactor impeller.

15. The process according to claim 10 wherein said reaction vessel has a height to diameter ratio of less than 1.4.

16. The process according to claim 10 wherein said reactor impeller is either a pitched blade turbine or a hydrofoil type turbine.

17. The process according to claim 10 wherein each said baffle has a width greater than 1/12th of the diameter of said reaction vessel; whereby each said baffle aids in minimizing surface turbulence and vortexing.

18. The process according to claim 1 wherein about 2.5 to about 20 volumes of reaction mixture are internally recirculated per minute.

19. The process according to claim 1 wherein about 3 to about 20 volumes of reaction mixture are internally recirculated per minute.

20. The process according to claim 1 further comprising at least one of the following additional steps:
   c. removal of excess acid by nitrogen or steam stripping;
   d. addition of an adsorbent selected from the group consisting of: alumina, silica gel, activated carbon, clay and/or filter aid to said ester mixture;
   e. addition of base to neutralize any residual organic acids;
   f. filtration of solids from said ester mixture containing the bulk of the excess alcohol or acid used in the esterification process;
   g. removal of said excess alcohol or acid from said ester mixture by steam or nitrogen stripping and recycling of said excess alcohol or acid to said reaction vessel; and
   h. removing any residual solids from the stripped ester by means of secondary filtration.

21. The process according to claim 20 further comprising the following step:
   i. removal of the water used in the hydrolysis step by settling and/or by means of flashing.

22. The process according to claim 21 wherein said esterification process is a batch process and the water removal step (i) is accomplished by dropping the pressure as rapidly as possible.

23. The process according to claim 20 wherein the addition of said adsorbent in step (d) may occur either before or after the stripping step (g).

24. The process according to claim 20 wherein said base in the neutralization step is a dilute solution of soda ash which contains soda ash in an amount of about 1.5 to about 2 times the stoichiometric acid value of the residual ester and said water is present in an amount from about 1.5 to about 6 percent of the crude ester weight.

25. The process according to claim 20 wherein said esterification process is a continuous process and said flash step occurs across a valve.

26. The process according to claim 21 wherein the water concentration after said water removal step (i) is in the range of about 150 to about 1000 ppm.

27. The process according to claim 1 wherein said heating step (b) further comprises:
   passing vapor from said reaction vessel through a packed tower or column such that a portion of alcohol contained within said vapor is stripped and recycled to said reaction vessel, and wherein the partially stripped vapor containing alcohol and water is taken overhead;
   passing said partially stripped vapors to an overhead collection drum which allows said alcohol and said water to separate into two liquid phases;
   separating said alcohol from said water;
   recycling said alcohol either to said packed tower and contacting it with said vapor from said reaction vessel or to exhaust;
   recycling said water to said hydrolysis step;
   taking overhead the vapors from said collection drum for condensation of water contained therein; and
   recycling condensate from said vapors to said hydrolysis step.

28. The process according to claim 1 wherein said heating step (b) further comprises:
   passing vapor from said reaction vessel to an overhead collection drum which allows the alcohol and the water contained within said vapor to separate into two liquid phases;
   separating said alcohol from said water;
   recycling said alcohol either to an alcohol flash drum thereby producing a water-rich vapor which is taken out overhead and combined with said vapors from said reaction vessel and an alcohol-rich liquid which is recycled to said reaction vessel;
   recycling said water to said hydrolysis step;
   taking overhead the vapors from said collection drum for condensation of water contained therein; and
   recycling condensate from said vapors to said hydrolysis step.

* * * * *